(12) United States Patent
Keppler et al.

(10) Patent No.: US 10,052,114 B2
(45) Date of Patent: Aug. 21, 2018

(54) SHOULDER BASE PLATE COVERAGE AND STABILITY

(71) Applicant: MATERIALISE N.V., Leuven (BE)

(72) Inventors: Louis J. Keppler, Pittsburgh, PA (US); Takehito Hananouchi, Hyogo (JP); Dieter Vangeneugden, Overpelt (BE)

(73) Assignee: Materialise, NV, Leuven (BE)

( * ) Notice: Subject to any disclaimer, the term of this patent is extended or adjusted under 35 U.S.C. 154(b) by 329 days.

(21) Appl. No.: 14/850,836

(22) Filed: Sep. 10, 2015

(65) Prior Publication Data

US 2016/0074052 A1 Mar. 17, 2016

Related U.S. Application Data

(63) Continuation-in-part of application No. 14/002,381, filed as application No. PCT/EP2012/071260 on Oct. 26, 2012, now abandoned, application No. 14/850,836, which is a continuation-in-part of application No. 13/180,688, filed on Jul. 12, 2011, and a continuation-in-part of application No. 14/131,218, filed as application No. PCT/EP2012/063676 on Jul. 12, 2012, now abandoned, which is a continuation of application No. 13/180,688, filed on Jul. 12, 2011.

(Continued)

(30) Foreign Application Priority Data

Jul. 12, 2011 (EP) ..................... 11173606

(51) Int. Cl.
*A61F 5/00* (2006.01)
*A61B 17/17* (2006.01)
*A61B 34/10* (2016.01)
*A61B 17/56* (2006.01)

(52) U.S. Cl.
CPC .... *A61B 17/1778* (2016.11); *A61B 2017/568* (2013.01); *A61B 2034/108* (2016.02); *Y10T 29/49* (2015.01); *Y10T 29/49771* (2015.01)

(58) Field of Classification Search
CPC combination set(s) only.
See application file for complete search history.

(56) References Cited

U.S. PATENT DOCUMENTS 3,919,772 A 11/1975 Lenczycki
4,646,729 A 3/1987 Kenna et al.
(Continued)

FOREIGN PATENT DOCUMENTS

EP 0353171 B1 1/1990
EP 1457159 A1 9/2004
(Continued)

OTHER PUBLICATIONS

International Search Report and Written Opinion dated Jan. 15, 2013 by the International Searching Authority, European Patent Office for related Intl. application PCT/EP2012/071260 filed on Oct. 26, 2012.

(Continued)

*Primary Examiner* — Sameh Boles
(74) *Attorney, Agent, or Firm* — Patterson & Sheridan LLP

(57) ABSTRACT

Provided herein are patient-specific surgical device that allow for a stable fitted position for use in shoulder surgery. The patient-specific surgical devices may have different functions such as a function as a guide.

15 Claims, 5 Drawing Sheets

Related U.S. Application Data

(60) Provisional application No. 61/552,595, filed on Oct. 28, 2011.

(56) References Cited

U.S. PATENT DOCUMENTS

| | | |
|---|---|---|
| 4,719,907 A | 1/1988 | Banko et al. |
| 5,141,680 A | 8/1992 | Almquist et al. |
| 5,192,539 A | 3/1993 | Van Der Marel et al. |
| 5,768,134 A | 6/1998 | Swaelens et al. |
| 5,976,149 A | 11/1999 | Masini |
| 6,273,891 B1 | 8/2001 | Masini |
| 6,416,553 B1 | 7/2002 | White et al. |
| 7,959,680 B2 | 6/2011 | Stone et al. |
| 7,981,158 B2 | 7/2011 | Fitz et al. |
| 8,038,719 B2 | 10/2011 | Gunther |
| 8,414,591 B2 | 4/2013 | De Smedt et al. |
| 8,608,749 B2 | 12/2013 | Meridew |
| 2004/0199258 A1 | 10/2004 | Macara |
| 2005/0148843 A1 | 7/2005 | Roose |
| 2005/0203528 A1 | 9/2005 | Couture et al. |
| 2006/0161167 A1 | 7/2006 | Myers et al. |
| 2008/0262499 A1 | 10/2008 | Giori |
| 2008/0269906 A1 | 10/2008 | Iannotti et al. |
| 2009/0318923 A1 | 12/2009 | Burkhart et al. |
| 2010/0016984 A1 | 1/2010 | Trabish |
| 2010/0016986 A1 | 1/2010 | Trabish |
| 2010/0023015 A1 | 1/2010 | Park |
| 2010/0082035 A1 | 4/2010 | Keefer |
| 2010/0087829 A1 | 4/2010 | Metzger et al. |
| 2011/0029088 A1 | 2/2011 | Rauscher et al. |
| 2011/0093086 A1 | 4/2011 | Witt et al. |
| 2011/0130795 A1 | 6/2011 | Ball |
| 2012/0022657 A1 | 1/2012 | Iannotti et al. |
| 2012/0078258 A1 | 3/2012 | Lo et al. |
| 2012/0109226 A1 | 5/2012 | Iannotti et al. |
| 2012/0143267 A1 | 6/2012 | Iannotti et al. |
| 2012/0179147 A1 | 7/2012 | Geebelen |
| 2012/0245647 A1 | 9/2012 | Kunz |
| 2013/0018378 A1 | 1/2013 | Hananouchi et al. |
| 2013/0066321 A1 | 3/2013 | Mannss et al. |
| 2013/0110116 A1 | 5/2013 | Kehres et al. |

FOREIGN PATENT DOCUMENTS

| | | |
|---|---|---|
| EP | 1486900 A1 | 12/2004 |
| EP | 2324780 A1 | 5/2011 |
| WO | 2008109751 A1 | 9/2008 |
| WO | 2010124164 A1 | 10/2010 |
| WO | 2011029911 A1 | 3/2011 |
| WO | 2011060536 A1 | 5/2011 |
| WO | 2011110374 A1 | 9/2011 |
| WO | 2013062848 A1 | 5/2013 |

OTHER PUBLICATIONS

International Preliminary Report on Patentability, dated Apr. 28, 2014 issued in connection with related Intl. application PCT/EP2012/071260 filed on Oct. 26, 2012.

International Preliminary Report on Patentability, dated Jan. 14, 2014 issued in connection with related PCT Application No. PCT/EP2012/063676, filed Jul. 12, 2012.

International Search Report, dated Dec. 10, 2012 issued in connection with related PCT Application No. PCT/EP2012/063676, filed Jul. 12, 2012.

SHOULDER BASE PLATE COVERAGE AND STABILITY

CROSS-REFERENCE TO RELATED APPLICATIONS

This application is continuation in part of co-pending U.S. patent application Ser. No. 14/002,381, filed Aug. 30, 2013, which is a U.S. national stage entry under 35 U.S.C. § 371 of PCT International Patent Application No. PCT/EP2012/071260, filed Oct. 26, 2012, which claims priority to U.S. Provisional Application No. 61/552,595, filed Oct. 28, 2011. This application is also a continuation in part of co-pending U.S. application Ser. No. 13/180,688, filed Jul. 12, 2011. This application is also a continuation in part of co-pending U.S. patent application Ser. No. 14/131,218, filed Jan. 7, 2014, which is a U.S. national stage entry under 35 U.S.C. § 371 of PCT International Patent Application No. PCT/EP2012/63676, filed Jul. 12, 2012, which claims priority to European Patent Application No. 11173606.2, filed Jul. 12, 2011 and which also claims priority to U.S. patent application Ser. No. 13/180,688, filed Jul. 12, 2011. Each of the above-referenced patent applications is hereby incorporated by reference in its entirety.

BACKGROUND OF THE INVENTION

Field of the Invention

Provided herein are patient-specific surgical devices that provide a stable fitted position for use in shoulder surgery, fitting within a typical surgical incision. The patient-specific surgical devices may be used for various purposes including for use as or with a shoulder guide.

Description of the Related Technology

Conventional orthopedic prostheses, guides and implants have been in use for many years with considerable success. The use of custom designed prostheses, guides and implant components based on the patient-specific anatomy has moreover overcome many shortcomings of the older designs. Such patient-specific devices can be developed using commercially available software. Typically such devices are used for orthopedic interventions to the spine, hip, shoulder, knee and/or radius. Patient-specific devices available on the market include patient-specific knee replacement prostheses, patient-specific femoral and tibia cutting blocks, distal radius drilling, cutting templates, etc. At present, there exists an increasing amount of surgical interventions that benefit from the use of these medical image based patient specific surgical devices as described in patent applications US 2005/0203528 A1 and EP 1 486 900 A1, for instance.

While patient-specific devices such as guides are now typically used to accurately place pins, guide bone cuts or insert implants during orthopedic procedures, the correct positioning of these patient-specific devices remains a critical factor with important impact on the outcome of the procedure.

Currently, the patient-specific surfaces of such devices are created based on surgical exposure, thereby assessing which anatomical features are accessible during the surgery. However, based on these features alone, the stability of the patient-specific device is relatively unknown. Typically, a multitude of patient-specific devices with different patient-specific surfaces are created by combining different sections of the patient's anatomy and subjectively evaluating the stability of each, thereby further developing the patient-specific device and improving the stability. This is a very inefficient method because the number of surface combinations that need to be assessed is high and the patient-specific devices, or at least a part thereof, need to be physically produced before the stability can be analyzed. Furthermore, the stability of these devices can only be measured on a subjective level whereas inter- and intra-user variability should also be taken into account when evaluating the guide surface combinations. Also the exact patient-specific surface varies for every patient such that typically a group of example anatomies is used to evaluate stability.

When performing medical and surgical procedures on and around the shoulder joint, and specifically on and around the glenoid, it is crucial to provide surgical instruments having a high accuracy and stability. Typical surgical instruments for these types of procedures utilize some of the anatomic regions of the glenoid, such as the anterior surface of the glenoid and the glenoid face. Retractors for these types of surgical procedures typically fit onto the posterior side of the glenoid as well. While the anterior surface of the glenoid and the glenoid face are commonly used for engaging with the surgical instruments, these anatomical regions do not provide the surgical tools with an acceptable accuracy and stability.

Accordingly, there is a need for improved patient-specific devices for performing shoulder surgery.

SUMMARY

Provided herein are patient-specific surgical devices having a stable fitted position on a shoulder bone, fitting within a typical surgical incision. These patient-specific surgical devices may be used for various purposes including for use as or with a shoulder guide. The patient-specific surgical devices as described herein comprise patient-specific contact elements, which fit onto areas on and/or around specific anatomical features of the glenoid and surrounding bone.

Also provided are methods for providing patient-specific devices which can be stably fitted into a typical surgical incision. These methods encompass designing the device to comprise contact surfaces with one or more of the neck of the coracoid process, the anterior surface of the glenoid and the surface of the glenoid face of the patient.

Starting from the fully exposed anatomy (available from images of the patient) and a given (i.e. desired) position for the functional feature based on preoperative planning, the surrounding anatomy of the glenoid can be analyzed, thereby determining the surface combinations on the bone providing the optimal stability for the patient-specific device. From the analysis of the stability, measures for the translational and rotational stability of the patient-specific device can be deduced Accordingly, a method has been developed which allows the identification of the surface combinations which provide the optimal stability given the surgical incision or the available surgical exposure.

The patient-specific surgical devices as described herein specifically comprise patient-specific elements interacting with or at least partially complementary with one or more of the neck of the coracoid process, the anterior surface of the glenoid and the surface of the glenoid face. More specifically, at least one of the patient-specific elements interacts with the surface of the glenoid face from "9-o'clock to 12-o'clock" on a left shoulder or "3-o'clock to 12-o'clock" on a right shoulder up until the location of the functional feature, such as a drill cylinder. More particularly, the devices are envisaged to comprise a patient-specific element which is at least partially complementary with the glenoid face from directly anterior to directly superior which corresponds to an angle of about 90 degrees.

In further particular embodiments the patient-specific devices as described herein are surgical patient-specific devices. More particularly said patient-specific device is a shoulder guide. In further particular embodiments the device is a shoulder base plate. In further particular embodiments the improved patient-specific devices are made by additive manufacturing.

Provided herein is a patient-specific surgical device providing a stable fit onto a shoulder one of a patient, comprising:
 a support structure;
 one or more dedicated functional features; and
 one or more patient-specific contact elements attached to part of said support structure, said patient-specific contact elements comprising a patient-specific surface which conforms to one or more anatomical features of the shoulder bone, wherein said one or more patient-specific elements conform to at least part of the neck of the coracoid process.

In a particular embodiment, said patient-specific surgical device further comprises one or more patient-specific elements at least partially conforming with anatomical features selected from the anterior surface of the glenoid and/or the surface of the glenoid face. In a particular embodiment, said patient-specific elements are at least partially complementary with the neck of the coracoid process, the anterior surface of the glenoid and the surface of the glenoid face.

In a particular embodiment, said patient-specific elements are at least partially complementary with the glenoid face from "9-o'clock to 12-o'clock" on a left shoulder or "3-o'clock to 12-o'clock" on a right shoulder extending as a circle segment to a functional feature for placement centrally in the glenoid fossa. More particularly, the devices are envisaged to comprise a patient-specific element which is at least partially complementary with the glenoid face from directly anterior to directly superior which is an angle of about 90 degrees.

In a particular embodiment, said patient-specific elements are at least partially complementary with the bone structure running down from the neck of the coracoid process towards the suprascapular notch.

In a particular embodiment, said one or more functional features are elements for guiding or positioning a functional tool or instrument such as a wire, a pin, a screw or a drill.

In a particular embodiment, said functional feature is an alignment element such as a wire or a pin In a particular embodiment, said patient-specific device is a shoulder guide In a particular embodiment, said patient-specific surgical device is manufactured at least in part via additive manufacturing.

Another embodiment pertains to a method for providing a patient-specific surgical device for positioning onto a shoulder anatomy of a patient, comprising:
 a) identifying and selecting, based on volume information of the shoulder anatomy from a patient, features of the bone on or surrounding the glenoid which are suitable for fitting patient-specific contact elements; and
 b) designing, based on the installation direction of said surgical device and the information obtained in step a) a surgical device, comprising:
  a support structure;
  one or more dedicated functional features; and
  one or more patient-specific contact elements linked to or forming an integral part of said support structure, each comprising a patient-specific surface which conforms with at least part of one or more features of areas on and/or around specific anatomical features of the glenoid, wherein said one or more patient-specific contact elements conform to at least part of the neck of the coracoid process.

More particularly, said selected parts of the bone surrounding the glenoid further comprises the anterior surface of the glenoid face.

In a particular embodiment, said selected parts of the bone surrounding the glenoid include the glenoid face from "9-o'clock to 12-o'clock" on a left shoulder or "3-o'clock to 12-o'clock" on a right shoulder extending optionally to the location of a functional feature. More particularly, the selected areas of the bone are part of the glenoid face from directly anterior to directly superior corresponding to an angle of about 90 degrees.

In a particular embodiment, the surrounding anatomy of the glenoid is analyzed, thereby determining the surface combinations providing the optimal stability for the patient-specific device.

More particularly, the analysis includes a measurement of the translational and rotational stability of the patient-specific device, thereby obtaining information about the stability of the device.

In a particular embodiment, said method includes defining or measuring the distance from the coracoid neck to the suprascapular notch and identifying and selecting a part of the bone structure surrounding the glenoid and running down the coracoid neck towards the suprascapular notch for designing a patient-specific contact element.

In some embodiments, the patient-specific devices comprise one or more patient-specific contact elements which fit onto areas on a socket of a ball-and-socket joint, onto areas around said socket and/or onto the rim of said socket in at least three contact points. Where the socket is a glenoid cavity, the areas around the socket may include the glenoidal rim and the periglenoidal region (e.g. infraglenoidal tuberculum, supraglenoidal tuberculum and collum scapulae, etc.) and might include the acromion and processus coracoideus (coracoid process). Where the socket is an acetabulum, the areas around the socket may include the periacetabular region (e.g. the limbus acetabuli, sulcus supraacetabularis, superior ramus, etc.). The contact points have an arrangement wherein the angle between the line connecting one contact point and the center of the circle or ellipse best fitting the socket rim and the line connecting the adjacent contact point and said center is never greater than 180°. The patient-specific devices further comprise a positioning element which is attached to the fixture. This positioning element is provided with one or more holes which allow the insertion of the alignment element. Additionally, the positioning element is detachable from the rest of the device.

In particular embodiments, one (of the) contact element(s) is positioned on the patient-specific device such that, when positioned on the bone, it interacts with an anatomical feature present on the rim of the socket or on the bone in or around the socket. In further embodiments, this anatomical feature is the posterior notch of the transverse ligament, or the coracoid process.

In certain embodiments, the patient-specific devices comprise at least two contact elements, or at least three contact elements. The contact elements then fit onto areas on the socket, around the socket and/or on the socket rim in at least three contact points, wherein the contact points have an arrangement wherein the angle between a line drawn between one contact point and the center of the circle or ellipse best fitting the socket rim and a line drawn between the adjacent contact point and said center is never greater than 180°. In further embodiments, the patient-specific device comprises at least two contact elements, wherein the positioning element corresponds to one of the contact elements.

Further embodiments are described herein below.

BRIEF DESCRIPTION OF THE DRAWINGS

The following description of the figures of specific embodiments is merely exemplary in nature and is not intended to limit the present teachings, their application or uses. Throughout the drawings, corresponding reference numerals indicate like or corresponding parts and features.

Figure 1A:
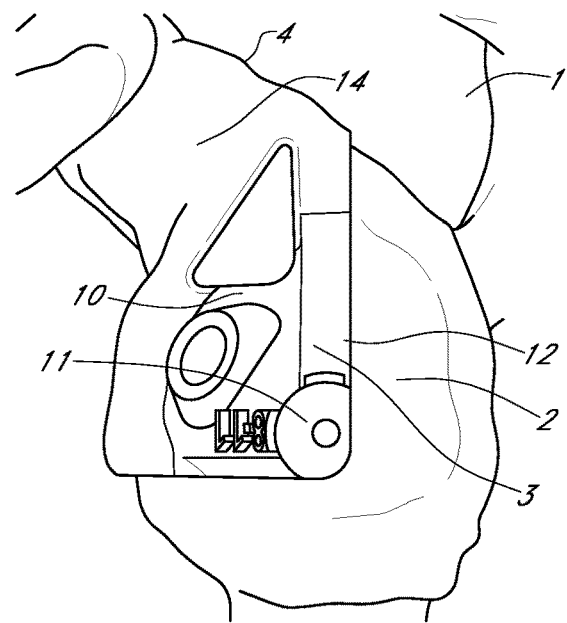
FIGS. 1A and 1B: Illustration of an embodiment of a patient-specific surgical guide positioned on the glenoid.

1—Shoulder joint; 2—glenoid; 3—patient-specific surgical guide; 4—neck of the coracoid process; 5—anterior surface of the glenoid; 10—support structure; 11—guiding feature; 12—contact element complementary to the surface of the glenoid face; 14—contact element complementary to the neck of the coracoid process; 15—contact element complementary to the anterior surface of the glenoid

DETAILED DESCRIPTION

The concepts provided herein are described with respect to particular embodiments but are not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of when referring to recited members, elements or method steps also include embodiments which "consist of said recited members, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform the same function. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in the description, including technical and scientific terms, have the meaning as commonly understood by one of ordinary skill in the art. By means of further guidance, definitions for the terms used in the description are included to better appreciate the teaching concepts provided herein. The terms or definitions used herein are provided solely to aid in the understanding thereof.

Reference throughout this specification to "one embodiment" or "an embodiment" means that a particular feature, structure or characteristic described in connection with the embodiment is included in at least one embodiment of the present as envisaged herein. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the teachings provided herein, and form different embodiments, as would be understood by those in the art. For example, in the following any of the described embodiments can be used in any combination.

In some embodiments, the devices and methods described herein relate to the field of implant surgery, more particularly surgical devices which are placed into a socket of a ball-and-socket joint. For human patients, this is an acetabular cup device and/or a glenoid device. The term "acetabular cup device" as used herein refers to the component of a prosthetic hip device which is placed into the acetabulum of a patient. The acetabulum is a concave surface of the pelvis, where the head of the femur meets with the pelvis, thus forming the hip joint. The term "glenoid device" as used herein refers to a component of a prosthetic shoulder device which is placed into or onto the glenoid cavity of a patient. Such devices may be used in a (total) shoulder arthroplasty or reverse (total) shoulder arthroplasty. The glenoid cavity, also known as glenoid fossa (of the scapula), is a shallow surface, which is located on the lateral angle of the scapula. This cavity forms the glenohumeral joint along with the humerus.

Provided herein is a patient-specific surgical device that provides a stable fitted position for use in shoulder surgery, fitting within a typical surgical incision.

As used herein, the term "patient-specific device" relates to any surgical, therapeutic or diagnostic device or tool such as an implant, a prosthesis or a surgical guide which is designed based on an individual patient's anatomy to include features which have a custom fit or perform a customized function for a specific location in a specific patient. The use of guides and implants which are patient-specific makes it possible to ensure an improved or optimized accuracy of the surgical intervention and an improved anatomical fit for prosthetic structures thereby ensuring optimized functionality for each patient. Even when such devices are used in combination with standard implants, tools, devices, surgical procedures, and/or other methods, important benefits in accuracy of placement can be obtained. Accordingly, the term "patient-specific device" is used to refer to a custom-made device specific to the individual patient's anatomy. More particularly, device is a device comprising at least one surface which conforms with or is complementary to at least part of the patient's anatomy.

The terms "surgical guiding tool" and "guiding tool" as used herein refer to (patient-specific) surgical tools that can be positioned onto an anatomical part of a patient and that help a surgeon in the accurate positioning of an alignment element and/or guidance of other surgical instruments, such as drilling or cutting tools. Thus, guiding tools typically comprise a "guiding element" which is a dedicated feature for guiding a positioning tool or cutting or drilling elements. Examples of guiding elements are detailed herein below.

In one embodiment, the relevant anatomical part is the shoulder bone, more particularly the glenoid cavity, the coracoid neck, and the bone surrounding it.

The glenoid cavity, also known as glenoid fossa (of the scapula), is a shallow surface, which is located on the lateral angle of the scapula. This cavity forms the glenohumeral joint along with the humerus. The part of the bone encompassing the glenoid cavity including the glenoid rim is also referred to herein as "the glenoid".

The patient-specific surgical device may be used for various purposes including for use as or with a shoulder guide.

The surgical device as described herein comprises a body or support structure and one or more positioning features, which allow positioning onto the shoulder bone and typically comprise contact elements linked to or forming an (integral) part of the body or support structure or the positioning features which allow a stable fitting on the shoulder anatomy or part thereof. The positioning feature may be reversibly connected to or form an integral part of the body of the surgical device as described herein, and is used for positioning the patient-specific contact elements onto or into the shoulder anatomy such as the glenoid in a pre-operatively planned position. In particular embodiments the positioning feature is a ridge which is formed by the body of the device over at least part of the rim of the glenoid cavity. Moreover, at least the devices as described herein are devices comprising at least one surface which conforms to or is complementary with at least part of the patient's anatomy. This surface is typically present on the body of the device and may also be part of the positioning features. The complementary surface is also referred herein as the "patient-specific element". In particular embodiments, the positioning features are provided as discrete positioning elements. In further embodiments these positioning elements are characterized in that they each comprise a patient-specific surface which conforms with and/or interacts with at least part of the neck of the coracoid process, the anterior surface of the glenoid and/or the surface of the glenoid face. These are referred to as patient-specific contact elements. It is further envisaged herein that the devices comprise two or more contact elements which are selected such that the combination of said two or more contact elements ensures a secure fit of said device when positioned onto the bone.

The patient-specific surgical device as described herein may optionally further comprise one or more dedicated functional features, the functional features being required during the surgical procedure for guiding or positioning functional elements. The functional features may be integrated in the remainder of the device but may also be removably connected thereto. These functional elements include, but are not limited to a wire, pin, screw or drill, drill sleeve or metal insert device, particularly a metal wire, pin, screw or drill.

Where the devices envisaged herein are guiding tools, they will comprise as functional features one or more guiding elements, which may be integrated in the remainder of the device but may also be removably connected thereto. In particular embodiments, the patient-specific surgical guide comprises a functional feature which is a guiding feature for a surgical instrument or tool such as, but not limited to a slot or a cylinder.

In particular embodiments, the patient-specific surgical guide comprises a functional feature which is an alignment element or a feature suitable for interaction with an alignment element.

In particular embodiments, the alignment element is a wire or a pin, particularly a Kirschner wire (K-wire), a Hoffmann pin or a drilling pin.

The functional features interacting with a surgical instrument or tool according to specific embodiments may include, but are not limited to guides or holes for interacting with tools and instruments such as wires, pins, screws or drills In particular embodiments, the surgical device may comprise one or more functional elements which are insertion elements which are reversibly connectable to the surgical device, particularly to the support structure. The insertion elements may comprise a guiding element for guiding a surgical operation, such as cutting, drilling, screwing, reshaping, reaming and implant positioning. In particular embodiments, the surgical device may comprise a first and a second insertion element, corresponding to a first surgical plan and a second (alternative) surgical plan. The different insertion elements may allow intra-operative switching between different pre-operatively planned surgical procedures.

In particular embodiments, the support structure or body comprises a handle. In certain embodiments, the handle bar may be used by the surgeon for positioning the device and/or for keeping the guide in a stable position.

In particular embodiments the relevant anatomical part of the shoulder onto which the patient-specific surgical device as defined herein is positioned is the glenoid, and more particularly the glenoid cavity and the bone surrounding it.

Typically the anatomy of the glenoid can be separated into a number of different anatomic surfaces defined by pre-defined borders based on anatomical conventions. Combinations of these surfaces are made to optimize stability, fit into the surgical incision, and to provide some visibility of the fit for verification through open windows.

The patient-specific surgical devices as described herein specifically comprise patient-specific elements (i.e. contact surfaces and positioning elements) interacting with or at least partially complementary with specific features of the glenoid. More particularly, the patient-specific elements interact with and/or are complementary to the neck of the coracoid process, the anterior surface of the glenoid and the surface of the glenoid face. More specifically, at least one of the patient-specific elements interacts with the surface of the glenoid face from "9-o'clock to 12-o'clock" on a left shoulder or "3-o'clock to 12-o'clock" on a right shoulder up until the location of the functional feature, such as a drill cylinder. More particularly, the devices are envisaged to comprise a patient-specific element which is at least partially complementary with the glenoid face from directly anterior to directly superior which corresponds to an angle of about 90 degrees.

For a given surgical incision and available surgical exposure, the combinations of patient-specific elements providing the optimal stability can be determined.

In particular embodiments the devices comprise one or more patient-specific elements which interact or are complementary to at least two or more, more particularly all three of these features of the glenoid. Typically, this is combined with patient-specific elements interacting with or complementary to other parts of the shoulder bone. The patient-specific elements can be separate elements interacting with different features or different features can interact with one patient-specific element extending to the different features. More particularly, the neck of the coracoid process can be used to obtain optimal stability of a shoulder device, as the combination of the neck of the coracoid process with the anterior surface of the glenoid and the surface of the glenoid face can provide an improved stability for patient-specific surgical devices.

The present disclosure particularly relates to the field of implant and/or guide surgery, more particularly implants and/or guides which are placed into a socket of a ball-and-socket joint, and typically the glenoid. For human patients, this is a glenoid implant and/or a glenoid guide.

The term "glenoid implant and/or guide" as used herein refers to a component of a prosthetic shoulder implant or guide which is placed into or onto the glenoid cavity of a patient. Such implants or guides may be used in a (total) shoulder arthroplasty or reverse (total) shoulder arthroplasty. The glenoid cavity, also known as glenoid fossa (of the scapula), is a shallow surface, which is located on the lateral angle of the scapula. This cavity forms the glenohumeral joint along with the humerus.

The devices envisaged herein may thus be used as surgical tools for facilitating the positioning of an implant and/or guide into or onto the glenoid in the body of an animal or human patient.

The surgical tools as described herein comprise one or more patient-specific elements interacting with or at least partially complementary with the neck of the coracoid process, the anterior surface of the glenoid and the surface of the glenoid face. These patient-specific elements can be contact surfaces and/or positioning features which are optionally combined. Whereas typical surgical instruments for shoulder surgery procedures utilize some of the anatomic regions of the glenoid such as the anterior surface of the glenoid and the glenoid face, one can optimize the stability of the patient-specific surgical instruments for performing surgical intervention of the shoulder joint with devices where one or more patient-specific elements interact with or are at least partially complementary with the neck of the coracoid process, the anterior surface of the glenoid and/or the surface of the glenoid face. In particular embodiments, interaction occurs with all three parts of the glenoid. In further embodiments, at least one of the patient-specific elements of the device interacts with the surface of the glenoid face from "9-o'clock to 12-o'clock" on a left shoulder or "3-o'clock to 12-o'clock" on a right shoulder, extending centrally into the glenoid cup. More particularly, the devices are envisaged to comprise a patient-specific element which is at least partially complementary with the glenoid face from directly anterior to directly superior which corresponds to an angle of about 90 degrees.

In other embodiments, the patient-specific element extends up until reaching the location of a functional feature, such as a drill cylinder, which can correspond essentially to the centre of the glenoid fossa.

Figure 1B:
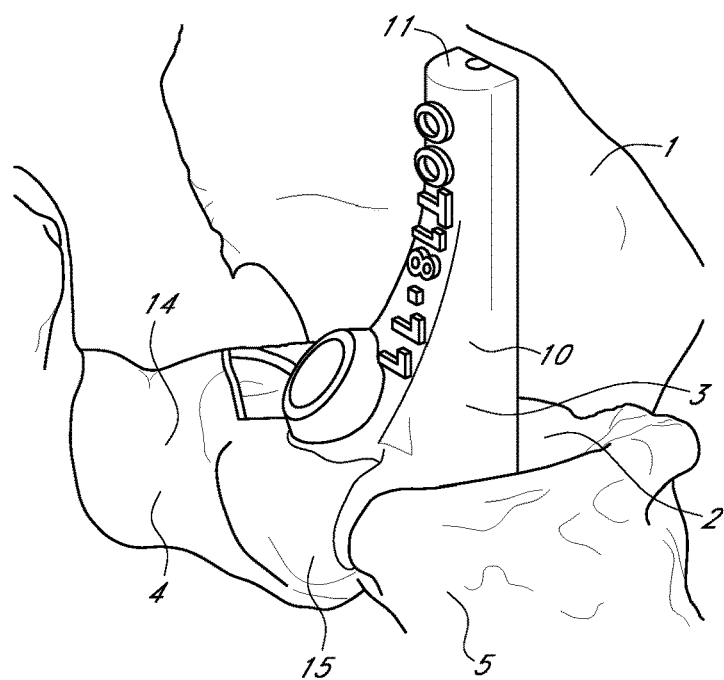

The device envisaged having the above features (of which an embodiment is illustrated in FIG. 1) is characterized by a body structure extending in a shape roughly corresponding to a right-angled triangle (corresponding essentially to a quarter circle of the glenoid face). More particularly, this body structure extends on the part corresponding to the hypotenuse of the triangle into a collar-like structure fitting the neck of the coracoid process. In particular embodiments, a functional feature such as a guiding feature is positioned on the body structure, more particularly in the corner formed by the right angle. In further particular embodiments, the guiding feature is a cylinder extending in a direction which is essentially perpendicular to the surface of the body structure, i.e. essentially parallel to the central axis of the glenoid fossa.

It will be understood to the skilled person that the body structure may but need not be a solid structure. In particular embodiments, the body structure may be an essentially continuous structure optionally comprising limited openings (which can serve as a visual aid during placement). The contact surface provided thereon for contacting with the bone may, but need not be continuous. In alternative embodiments, the body structure may be a set of beams which interconnect positioning elements designed to interact with specific parts of the bone. Such positioning elements can for instance comprise a structure extending over the rim of the glenoid, a structure extending in part over the collar of the coracoid process and a structure for placement centrally in the glenoid fossa (e.g. comprising a guiding element). In such an embodiment, each of the discrete positioning elements will have a patient-specific contact surface.

This specific combination provides the surgical devices with improved stability and accuracy, thereby ensuring a stable and unique fit position of the device on the glenoid. By providing patient-specific elements which fit onto at least three specific areas on and around the glenoid, it is ensured that the surgical tools is positioned onto the socket with an optimal rotational and translational stability, and this specifically according to pre-operational planning.

It has been found that surgical devices for positioning on the glenoid can be provided with an optimal stability and a high accuracy by using specific anatomical structures supports, thereby providing much more stable devices which are more easily positioned in their accurate position. With this aim, patient-specific instruments are provided, which are characterized by the presence of patient-specific elements which are complementary with specific anatomical features. These provide the guide with the required accuracy and stability. When selecting these features it should of course be ensured that the chosen anatomical locations are reachable during surgery as a support location.

The surgical devices such as guides envisaged herein are designed to ensure a restriction of movement of the device in both translational and rotational directions of the guide after placement on the glenoid. In addition, by the provision of patient-specific elements, they make it easier for the guide to be uniquely positioned onto the glenoid in a repeatable way. The patient-specific surgical devices envisaged herein can be based on accurate medical image planning, thereby determining very accurately the entry point and the best axis direction.

Also provided herein are methods for the design and manufacture of surgical devices for positioning on the shoulder.

The surgical devices as described herein comprise patient-specific contact elements such as positioning elements and/or contact surfaces. The generation of patient-specific surgical devices is done based on pre-operative images of the anatomy surrounding the glenoid, and planning of the surgery. During planning of the surgery, the installation direction and, where appropriate, the required position and orientation of guiding elements of the surgical device is determined. More particularly, the generation of patient-specific surgical tools is done based on pre-operative images of the glenoid and planning of the surgery.

The methods for producing the surgical tools as envisaged herein typically comprise the steps of:
a) identifying and selecting, based on volume information of the glenoid from a patient, features of the bone on or surrounding the glenoid which are suitable for fitting patient-specific contact elements; and
b) designing, based on the installation direction of said surgical device and the information obtained in step a), a surgical device comprising one or more patient-specific elements fitting onto specific parts of the bone of the glenoid and ensuring a stable fit of the device thereon.

In particular embodiments, the method as defined herein further comprises a step of identifying and selecting parts of the glenoid and the bone surrounding the glenoid which are suitable as support for a patient-specific element, wherein said selected parts include one or more parts selected from the group of the neck of the coracoid process, the anterior surface of the glenoid and the surface of the glenoid face. More particularly, the identified and selected parts of the glenoid and the bone surrounding the glenoid include the neck of the coracoid process and one or more parts selected from the anterior surface of the glenoid and/or the surface of the glenoid face. More particularly, the identified and selected parts of the glenoid and the bone surrounding the glenoid comprise or consist of the neck of the coracoid process, the anterior surface of the glenoid and the surface of the glenoid face.

In particular embodiments, the methods may also comprise the steps of obtaining said relevant information for the design of the devices envisaged herein. Accordingly, methods for developing the surgical tools as described herein may comprise the steps of:
a1) obtaining volume information of the glenoid from a patient; and;
a2) obtaining the installation direction of a glenoid implant or guide for said patient;
b) identifying and selecting parts of the glenoid and bone surrounding the glenoid which are suitable as support for a patient-specific element, wherein said selected parts include one or more parts selected from the group of the neck of the coracoid process, the anterior surface of the glenoid and the surface of the glenoid face, and preferably the glenoid face from "9-o'clock to 12-o'clock" on a left shoulder or "3-o'clock to 12-o'clock" on a right shoulder extending to the centre of the glenoid fossa in a triangle (or corresponding to an angle of about 90° extending from directly anterior to directly superior), optionally up until the location of a functional feature; and;
c) designing and optionally producing a surgical guiding tool based on the information obtained in steps a1), a2) and b) comprising one or more patient-specific elements fitting onto specific parts of the bone of the glenoid and ensuring a stable fit of the device thereon.

The step of obtaining volume information typically comprises obtaining digital patient-specific image information which can be done by any suitable means known in the art, such as for example X-ray images, a computer tomography (CT) scanner, a magnetic resonance imaging (MRI) scanner, an ultrasound scanner, or a combination of Roentgenograms. A summary of medical imaging has been described in "Fundamentals of Medical imaging", by P. Suetens, Cambridge University Press, 2002.

In particular embodiments, the methods can include defining or measuring the distance from the coracoid neck to the suprascapular notch and identifying and selecting a part of the bone structure surrounding the glenoid and running down the coracoid neck towards the suprascapular notch as support for a patient-specific element. In particular embodiments, a contact element can be designed which comprises at least part of the bone structure running down the coracoid neck towards the suprascapular notch. In further embodiments, the methods can comprise selecting at least 25% of the measured distance between the top of the coracoid neck and the suprascapular notch. More particularly, the contact element extends over at least 30%, 40%, 50%, 60%, 70%, 80% or 90% of the measured distance. In other embodiments the positioning element can be designed such that it comprises a positioning element extending along the coracoid neck towards the suprascapular notch ensuring a particular undercut angle. In particular embodiments, the undercut is at an angle of between 0 and 25°. This can further increase the stability of the device when placed on the bone. In particular embodiments the one or more parts of the glenoid selected for the design of contact elements can include the coracoid process. In further particular embodiments the selected parts can be a combination of part of the neck of the coracoid process, the anterior surface of the glenoid and the surface of the glenoid face, i.e. patient-specific elements are designed which contact and optionally interact with at least part of each of these parts of the glenoid.

The step of identifying and selecting parts of the glenoid and bone surrounding the glenoid which are suitable as patient-specific elements is based on determining optimal stability for the device taking into account the surgical window.

The methods envisaged herein thus comprise identifying and selecting parts of the bone on and/or surrounding the glenoid which are suitable for fitting patient-specific elements. This selection step will be based on a number of criteria which may include one or more of the following
the position of the part relative to the glenoid and the envisaged positioning of the device;
the shape and/or surface of the part, more particularly with regard to providing a patient-specific outline based on which a specific fit can be ensured;
the rigidity of the part;
the accessibility of the part during surgery and more particularly for positioning a device thereon.

The methods also encompass the step of designing the device based on the suitable parts of the glenoid identified and the installation direction of the device, i.e. the surgical planning. More particularly, the step of designing will encompass determining the positioning of one or more, typically two or more positioning elements, wherein the positioning element or the combination of the two or more patient-specific positioning elements ensures a specific and secure fit of the device when positioned onto the bone. This design will typically be based on the requirement that the one or more positioning elements ensure an accurate positioning of the device (by allowing only one correct fit)

and/or restrict the freedom of movement of the device after positioning correctly on the bone. In particular embodiments, as detailed above, ensuring a secure fit implies ensuring that both translational and rotational movement of the device is restricted when fitting of the positioning elements on the bone. In particular embodiments, the positioning elements are designed such that they clamp around the outside of the glenoid rim. In particular embodiments, this can be achieved by two discrete positioning elements envisaged to interact with the exterior bone surface of the glenoid rim on opposing sides of the glenoid cavity. In alternative embodiments these positioning features are integrated in one central body structure. In particular embodiments, the design includes the provision of a hinge in one or more of the positioning elements to allow placement of the device over the rim. A further aspect of the design encompasses determining the appropriate position and orientation of the functional element, such as the guiding element on the device.

Typically in the methods as described herein, the device is to be located within a surgical exposure, which also influences this selection.

Provided herein in particular embodiments are methods for producing the surgical tools as described which comprise the steps described above and further provide the step of manufacturing the device based on the design obtained. In a particular embodiment, Additive Manufacturing (AM) techniques are used for manufacturing the surgical guiding tools as described herein, or parts thereof. AM techniques are particularly useful to manufacture patient-specific contact surfaces, or to produce the surgical guiding tools in one piece. As an example, the manufacturing of medical-image-based patient-specific surgical instruments via AM is described in U.S. Pat. No. 5,768,134 (Swaelens et al).

AM can be defined as a group of techniques used to fabricate a tangible model of an object typically using three-dimensional (3-D) computer aided design (CAD) data of the object. Currently, a multitude of Additive Manufacturing techniques is available, including stereolithography, Selective Laser Sintering, Fused Deposition Modeling, foil-based techniques, etc.

Selective laser sintering uses a high power laser or another focused heat source to sinter or weld small particles of plastic, metal, or ceramic powders into a mass representing the 3-dimensional object to be formed.

Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object. Such a technique is described in U.S. Pat. No. 5,192,539.

Typically AM techniques start from a digital representation of the 3-D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer aided design and manufacturing (CAD/CAM) software.

The surgical guiding tools as described herein may be manufactured in different materials. Typically, only materials that are biocompatible (e.g. USP class VI compatible) with the animal or human body are taken into account. Preferably the surgical guiding tool is formed from a heat-tolerable material allowing it to tolerate high-temperature sterilization. In the case selective laser sintering is used as an AM technique, the surgical template may be fabricated from a polyamide such as PA 2200 as supplied by EOS, Munich, Germany or any other material known by those skilled in the art may also be used.

Also provided herein are methods wherein the stability of a patient-specific device is determined according to information regarding the combinations of anatomical regions, thereby providing a stability score within a desired range. This range is defined such that the patient-specific device can be placed and removed from the anatomical site while still providing a stable fit. For the present purpose, the methods described herein are specifically useful in the analysis and design of patient-specific devices for use on the shoulder joint and even more specifically towards patient-specific devices positioned on or around the glenoid. However, the methods can also be used for other types or surgical procedures and patient-specific devices used for other surgical procedures.

The analysis of the stability of patient-specific devices as described herein is determined by calculating the translational and rotational stability of the device and comparing these data to known stable and unstable surfaces. For instance, a guide fit which encompasses an entire cube would have the highest stability score, but could not be placed on or removed from the fitting cube. On the other extreme, a guide placed on a small section of a sphere would have many degrees of freedom and but would result in an unstable fit. For the sphere, however, increasing the surface area such that it covers at least half of the surface would further constrain translational stability. Therefore the type of surface along with the amount of surface coverage used determines the relative stability of the guide.

Depending on the surgical procedure, stability characteristics in some directions are more critical than others. These critical directions are determined by the required accuracy of the functional elements that are present on the patient-specific device and the surgical accuracy that needs to be obtained.

The analysis method is applied to the glenoid surface for use with guiding the direction of patient-specific device such as a shoulder guide in the context of the placement of a glenoid baseplate. Examining only the traditional surgical exposure, an appropriate stability could not be achieved using only the glenoid face and less than 3 cm of anterior glenoid ridge. Posterior and inferior regions of the glenoid ridge were examined up to 1 cm of fit region, but as these regions are obstructed by retractors or are difficult to access through the surgical incision these regions could not be reliably used to produce a stable fit. The neck of the coracoid process was then introduced as a possible fit region since this area could be used for a guide fit region even though its surface is not typically exposed during shoulder surgery. The following region combinations provided a stability which could accurately place the guide's functional element of the glenoid baseplate pin:

the surface of the coracoid neck preferably in the inferior/superior direction until the coracoid process makes an angular turn of more than 70 degrees.

the coracoid process and the direction thereof can optionally be used to determine xyz instead of anatomical planes since the direction of the coracoid neck with regard to the glenoid is a highly patient-specific feature.

along the anterior/posterior direction of the coracoid neck, the surface or part thereof may be used on either side thereby improving the rotational stability. This can optionally be further refined by the inherent angle of the neck of the coracoid process. Steeper neck angles typically require less surface area to be used.

the ideal placement of the posterior retractor such that the forces pull the guide into fit.

While the disclosure has been shown and described with reference to particular embodiments, it will be understood by those skilled in the art that various changes or modifications in form and detail may be made without departing from the scope and spirit of this disclosure.

Further illustrations of particular embodiments are provided herewith.

EXAMPLES

Figure 2A:
FIGS. 2A and 2B: Illustration of the glenoid, indicating the neck of the coracoid process.
Figure 2B:
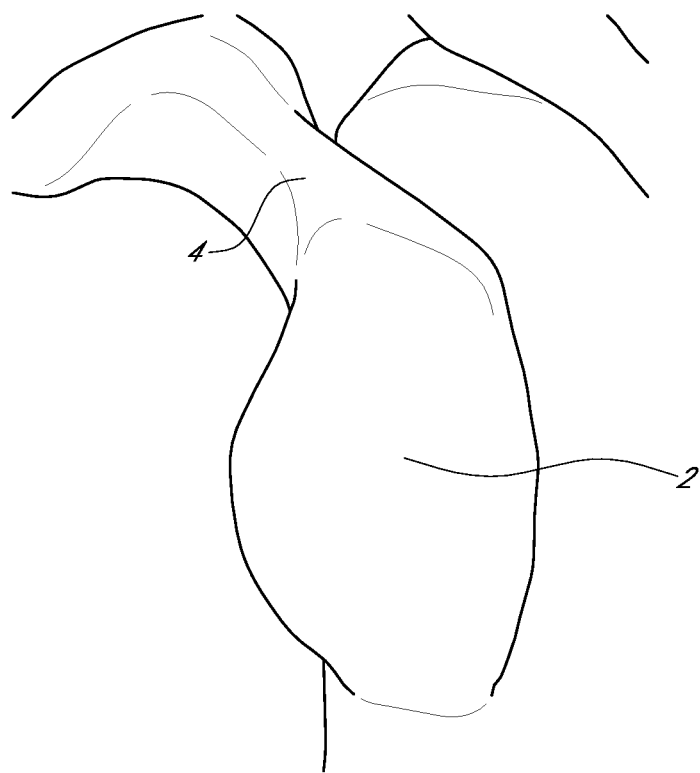

The following examples relate to patient-specific instruments for shoulder surgery. FIG. 1 illustrates a patient-specific surgical guide positioned on the glenoid. FIGS. 1 A and B illustrate a shoulder joint (1) with particular anatomical features including the glenoid (2), the neck of the coracoid process (4) and the anterior surface of the glenoid (5). Onto the shoulder joint (1) a patient-specific surgical guide (3) is positioned. The patient-specific surgical guide (3) comprises a support structure (10), a guiding feature (11) and several patient-specific contact elements including a contact element at least partially complementary to the surface of the glenoid face (12), a contact element at least partially complementary to the neck of the coracoid process (14) and a contact element at least partially complementary to the anterior surface of the glenoid (15). FIG. 2 illustrates a shoulder joint (1) with particular anatomical features including the glenoid (2), the neck of the coracoid process (4) and the anterior surface of the glenoid (5).

Figure 3A:
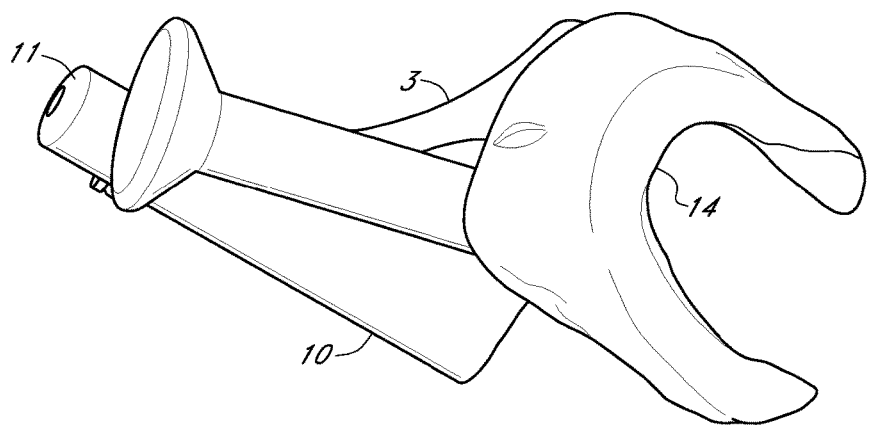
FIGS. 3A and 3B: Illustration of a patient-specific surgical guide according to a particular embodiment.
Figure 3B:
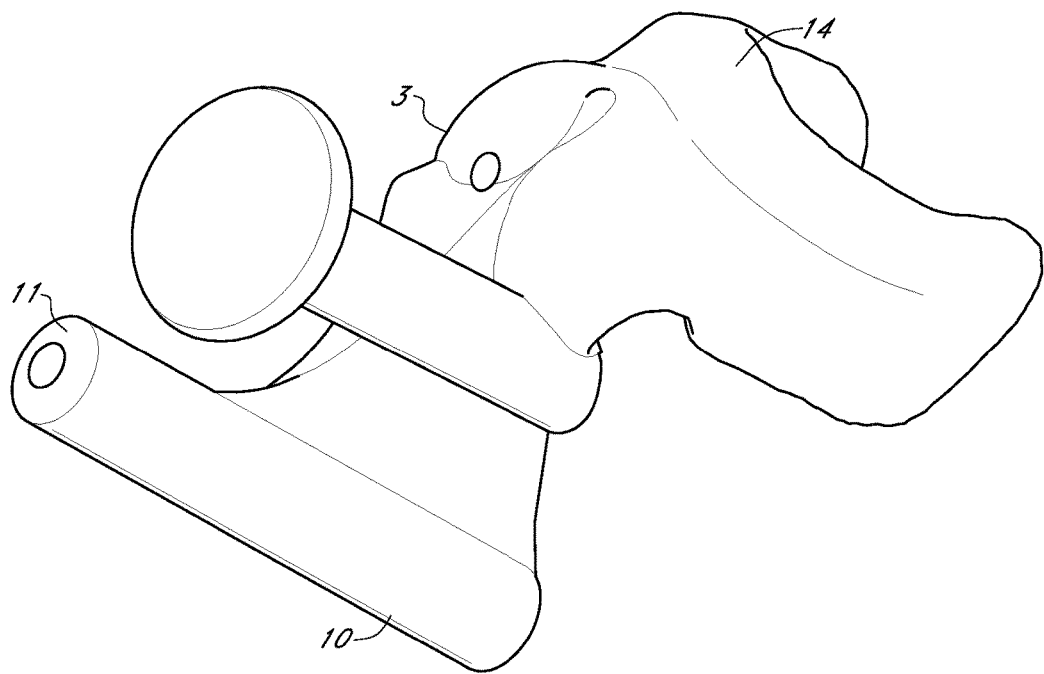

FIG. 3 illustrates a patient-specific surgical guide according to particular embodiments. The patient-specific surgical guide (3) comprises a support structure (10), a guiding feature (11) and several patient-specific contact elements including a contact element at least partially complementary to the surface of the glenoid face (12), a contact element at least partially complementary to the neck of the coracoid process (14) and a contact element at least partially complementary to the anterior surface of the glenoid (15).

Figure 4A:
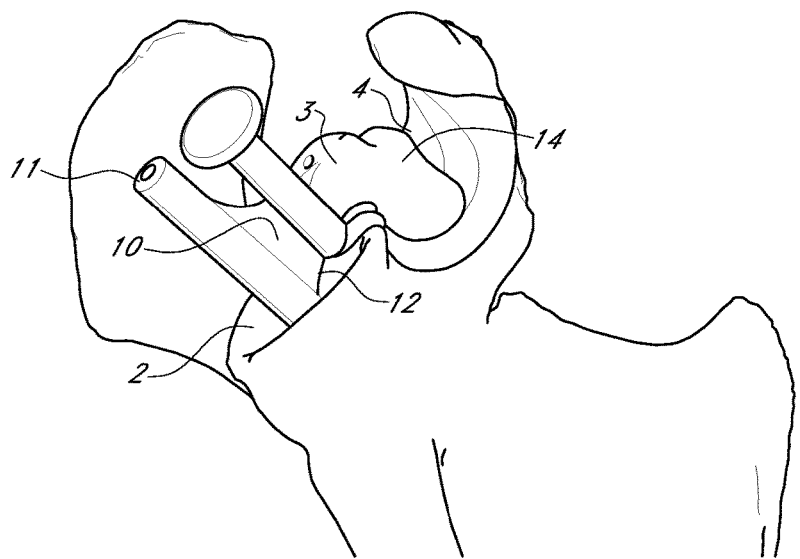
FIGS. 4A and 4B: Illustration of an embodiment of a patient-specific surgical guide positioned on the glenoid.
Figure 4B:
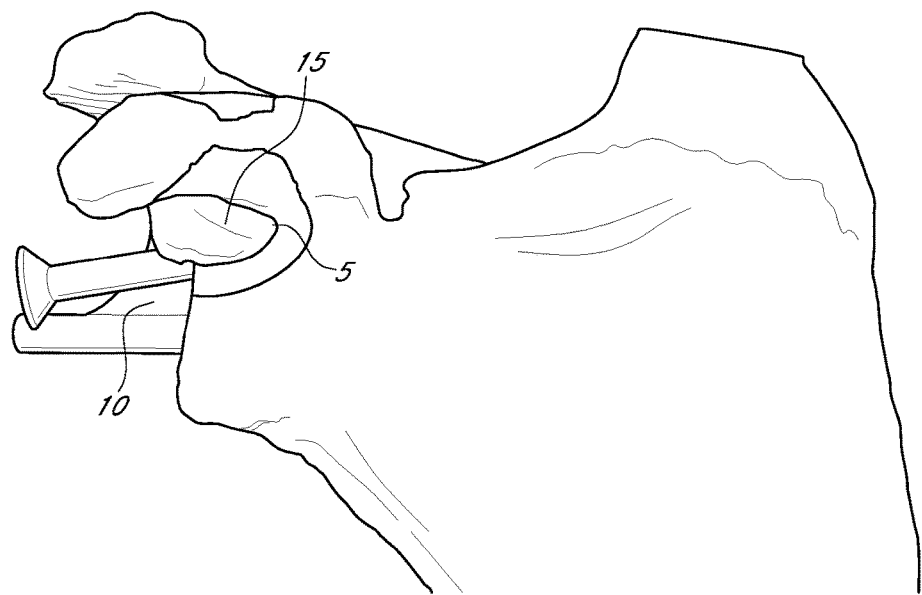
Figure 5:
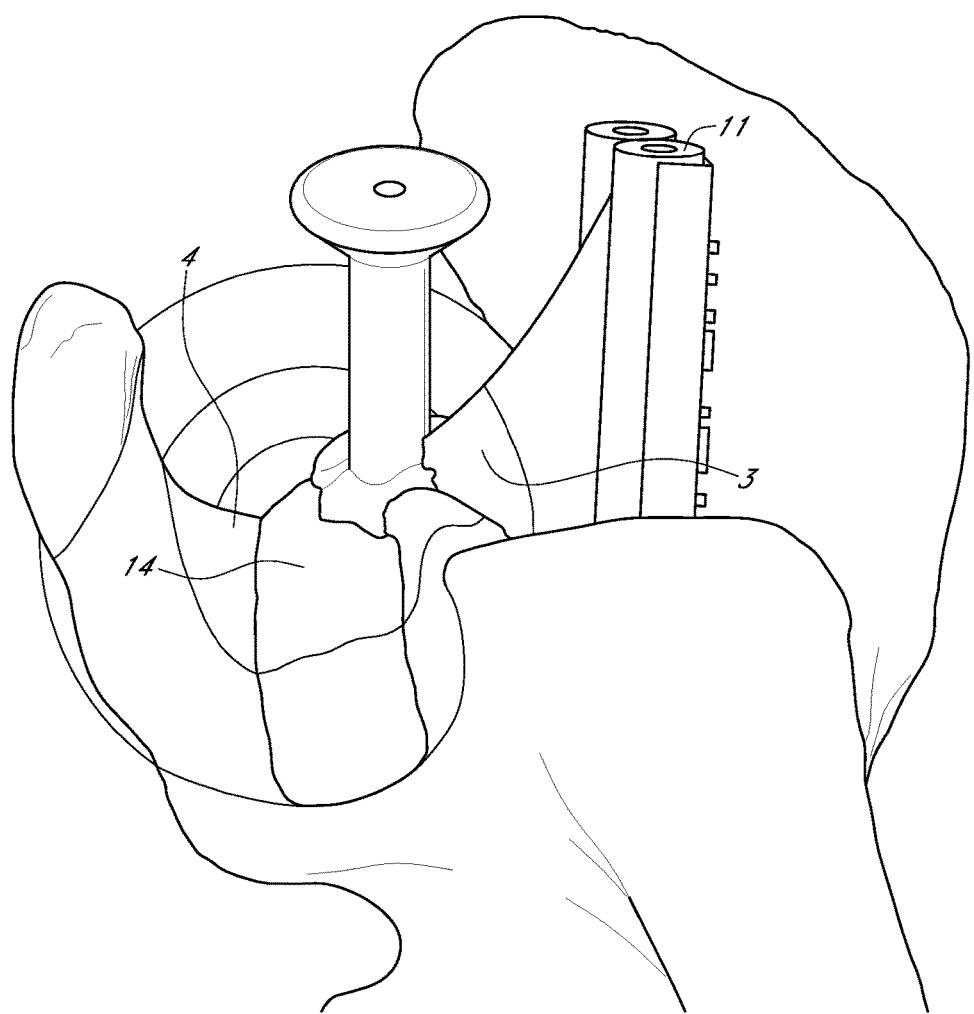
FIG. 5: Illustration of an embodiment of a patient-specific surgical guide positioned on the glenoid.

FIG. 4 illustrates a patient-specific surgical guide positioned on the glenoid. FIGS. 4 A and B illustrate a shoulder joint with particular anatomical features including the glenoid (2), the neck of the coracoid process (4) and the anterior surface of the glenoid (5). Onto the shoulder joint a patient-specific surgical guide (3) is positioned. The patient-specific surgical guide (3) comprises a support structure (10), a guiding feature (11) and several patient-specific contact elements including a contact element at least partially complementary to the surface of the glenoid face (12), a contact element at least partially complementary to the neck of the coracoid process (14) and a contact element at least partially complementary to the anterior surface of the glenoid (15). FIG. 5 illustrates a patient-specific surgical guide positioned on the glenoid. Onto the shoulder joint a patient-specific surgical guide (3) is positioned. The patient-specific surgical guide (3) comprises a support structure (10), two guiding features (11) and several patient-specific contact elements including a contact element at least partially complementary to the neck of the coracoid process (14).

What is claimed is:

1. A patient-specific surgical device providing a stable fit onto a shoulder anatomy of a patient, wherein the shoulder anatomy comprises a neck of a coracoid process and a glenoid comprising an anterior surface of the glenoid, the patient-specific surgical device comprising:
   a support structure;
   one or more dedicated functional features; and
   one or more patient-specific contact elements attached to a part of the support structure, the patient-specific contact elements comprising at least one patient-specific surface shaped to conform to one or more anatomical features of the shoulder anatomy,
   wherein the one or more anatomical features comprise at least part of the neck of the coracoid process.

2. The patient-specific surgical device according to claim 1, wherein the one or more anatomical features further comprise at least one of the anterior surface of the glenoid and a surface of a face of the glenoid.

3. The patient-specific surgical device according to claim 1, wherein the one or more anatomical features further comprise the anterior surface of the glenoid and a surface of a face of the glenoid.

4. The patient-specific surgical device according to claim 1, wherein said patient-specific contact elements are adapted to be at least partially complementary with a region of a rim of the glenoid over an angle of 90° extending as a circle segment centrally in the glenoid.

5. The patient-specific surgical device according to claim 1, wherein the shoulder anatomy includes a suprascapular notch, and wherein said patient-specific contact elements are adapted to be at least partially complementary with a joint structure running down from the neck of the coracoid process towards the suprascapular notch.

6. The patient-specific surgical device according to claim 1, wherein said one or more dedicated functional features comprise elements for guiding or positioning a functional tool or instrument such as a wire, a pin, a screw or a drill.

7. The patient-specific surgical device according to claim 1, wherein said one or more dedicated functional features comprise an alignment element such as a wire or a pin.

8. The patient-specific surgical device according to claim 1, wherein said patient-specific surgical device comprises a shoulder guide.

9. The patient-specific surgical device according to claim 1, wherein said patient-specific surgical device is manufactured at least in part via additive manufacturing.

10. A method for providing a patient-specific surgical device for positioning onto a shoulder anatomy of a patient, wherein the shoulder anatomy includes a neck of a coracoid process and a glenoid comprising an anterior surface of the glenoid comprising:
   identifying and selecting, based on volume information of the shoulder anatomy from the patient, features of the shoulder anatomy on or surrounding the glenoid which are suitable for fitting patient-specific contact elements; and
   designing, based on an installation direction of said patient-specific surgical device and the volume information, the patient-specific surgical device comprising:
      a support structure;
      one or more dedicated functional features; and
      one or more patient-specific contact elements linked to or forming an integral part of said support structure, each of the one or more patient-specific contact elements comprising a patient-specific surface which is adapted to conform with at least part of the features of the shoulder anatomy on or surrounding the glenoid, wherein the features comprise at least part of the neck of the coracoid process.

11. The method of claim 10, wherein the features of the shoulder anatomy on or surrounding the glenoid comprise at least one of the anterior surface of the glenoid and a surface of a face of the glenoid.

12. The method of claim 10, wherein the features of the shoulder anatomy on or surrounding the glenoid comprise a face of the glenoid from an angle of about 90 degrees extending from directly anterior to the glenoid face to directly superior to the glenoid face extending to the center of a cavity of the glenoid.

13. The method of claim 10, further comprising analyzing the shoulder anatomy on or surrounding the glenoid to determine a surface combination providing optimal stability for the patient-specific device.

14. The method of claim 13, wherein the analyzing comprises measuring a translational and rotational stability of the patient-specific device, thereby obtaining information about a stability of the device.

15. The method of claim 10, wherein the shoulder anatomy includes a suprascapular notch, and wherein said method includes defining or measuring a distance from the neck of the coracoid process to the suprascapular notch and wherein the features comprise a feature running down the coracoid neck towards the suprascapular notch.

\* \* \* \* \*